(12) United States Patent
Kamins et al.

(10) Patent No.: US 7,719,678 B2
(45) Date of Patent: May 18, 2010

(54) NANOWIRE CONFIGURED TO COUPLE ELECTROMAGNETIC RADIATION TO SELECTED GUIDED WAVE, DEVICES USING SAME, AND METHODS OF FABRICATING SAME

(75) Inventors: Theodore I. Kamins, Palo Alto, CA (US); Alexandre M. Bratkovski, Mountain View, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 359 days.

(21) Appl. No.: 11/796,011

(22) Filed: Apr. 25, 2007

(65) Prior Publication Data

US 2008/0266556 A1 Oct. 30, 2008

(51) Int. Cl.
*G01J 3/44* (2006.01)
*G01N 21/65* (2006.01)
(52) U.S. Cl. ................... 356/301; 977/765; 977/954
(58) Field of Classification Search .......... 356/301
See application file for complete search history.

(56) References Cited

U.S. PATENT DOCUMENTS

| 7,402,531 | B1 * | 7/2008 | Kuekes et al. .......... 356/301 |
| 2007/0177139 | A1 * | 8/2007 | Kamins et al. .......... 356/301 |

FOREIGN PATENT DOCUMENTS

WO    WO 03/083949 A1  *  10/2003
WO    WO 2004/046021 A1  *  6/2004

OTHER PUBLICATIONS

Zayats, Anatoly V., et al., "Nano-optics of surface plasmon polaritons", Physics Reports, 2005, pp. 131-314.
Hsu, Yung-Jung, et al., "Vapor-Solid Growth of Sn Nanowires: Growth Mechanism and Superconductivity", J. Phys. Chem., Feb. 12, 2005, Vol. 109, pp. 4398-4403.
Ou, Fung Suong, et al., "Multisegmented one-dimensional hybrid structures of carbon nanotubes and metal nanowires", Appl. Phys. Lett., 2006, Vo. 89, pp. 243122-1-243122-3.
Schmitt, Andrew L., "Synthesis and Properties of Single-Crystal FeSi Nanowires", Nano Lett., Mar. 10, 2006, vol. 6, No. 8, pp. 1617-1621.
Gole, J.L., et al., Direct synthesis of silicon nanowires, silica nanospheres, and wire-like nanospere agglomerates, Appl. Phys. Lett, Apr. 24, 2000, vol. 76, No. 17, pp. 2346-2348.

(Continued)

*Primary Examiner*—F. L Evans

(57) ABSTRACT

Various aspects of the present invention are directed to a nanowire configured to couple electromagnetic radiation to a selected guided wave and devices incorporating such nanowires. In one aspect of the present invention, a nanowire structure includes a substrate and at least one nanowire attached to the substrate. A diameter, composition, or both may vary generally periodically along a length of the at least one nanowire. A coating may cover at least part of a circumferential surface of the at least one nanowire. The nanowire structure may be incorporated in a device including at least one optical-to-electrical converter operable to convert a guided wave propagating along the length of the at least one nanowire, at least in part responsive to irradiation, to an electrical signal. Other aspects of the present invention are directed to methods of fabricating nanowires structured to support guided waves.

23 Claims, 13 Drawing Sheets

OTHER PUBLICATIONS

Peng, H.Y. et al., "Bulk-quantity Si nanosphere chains prepared from semi-infinite length Si nanowires", Journal of Applied Physics, Jan. 1, 2001, vol. 89, No. 1, pp. 727-731.

Wu, Yiying et al., "Block-by-Block Growth of Single-Crystalline Si/SiGe Superlattice Nanowires", Am. Chemical Society, 2002, vol. 2, No. 2, pp. 83-86.

Björk, M. T., et al., "One-dimensional Steeplechase for Electrons Realized", Am. Chemical Society, 2002, vol. 2, No. 2, pp. 87-89.

Ross, F.M., et al., "Sawtooth Faceting in Silicon Nanowires", The American Physical Society, Sep. 30, 2005, Prl. 95, pp. 146104-1-146104-4.

Kolb, Florian M., et al., "Periodic chains of gold nanoparticles and the role of oxygen during the growth of silicon nanowires", Appl. Phys. Lett., 2006, vol. 89, pp. 17311-1-17311-3.

* cited by examiner

NANOWIRE CONFIGURED TO COUPLE ELECTROMAGNETIC RADIATION TO SELECTED GUIDED WAVE, DEVICES USING SAME, AND METHODS OF FABRICATING SAME

TECHNICAL FIELD

Embodiments of the present invention relate generally to a nanowire configured to couple electromagnetic radiation to a selected guided wave and a device utilizing such a nanowire.

BACKGROUND

Guided waves ("GWs") have long been of scientific and practical interest. GWs include surface-plasmon-polariton ("SPP") waves and electromagnetic waves that propagate within waveguides, such as optical fibers and other dielectric or semiconductor waveguides. A SPP is an electromagnetic excitation with an electromagnetic field that propagates along an interface between a material with a negative dielectric constant, such as a metal, and a medium having a real, positive dielectric constant. A SPP is generated as a result of coupling a photon to a surface plasmon of the material with the negative dielectric constant. A plasmon is a quantum of the collective excitation of free electrons in a solid.

As shown in FIG. 1, a SPP wave 100 may be excited in a metal 102 having a dielectric constant $\in_m$ by irradiating the metal 102 with electromagnetic radiation using a number of different illumination configurations. The SPP wave 100 propagates along an interface 102 between the metal 104 and surrounding dielectric medium 106 (e.g., air) having a real, positive dielectric constant $\in_s$. Because the SPP wave 100 is concentrated at the interface 102, the intensity of the SPP wave 100 may be two to three times the intensity of the electromagnetic radiation used to excite the SPP wave 100. Due to Ohmic losses in the metal 104, the intensity of the SPP wave 100 decays exponentially during propagation along the interface 102.

Free-space light cannot be directly coupled into surface plasmons of the metal 102 due a mismatch between the dispersion relations for the SPP wave 100 and incident photons. In other words, the free-space light and the surface plasmons exhibit different wave momenta at the same frequency. A number of different excitation configurations have been developed to couple free-space light into surface plasmons of the metal 104. One of the more common SPP excitation configurations is the so-called Kretschmann geometry in which a prism is used match the photon and SPP wavevectors. Some other common SPP excitation configurations include forming a diffraction grating in the metal 104 or roughening the interface 102 of the metal 104 to provide a similar diffraction effect.

The enhanced intensity of a SPP wave may be used in a number of different applications. For example, surface enhanced Raman spectroscopy ("SERS") is a well-known spectroscopic technique for performing chemical analysis. In SERS, high-intensity electromagnetic radiation irradiates a specially prepared, nanostructured metal surface. A sample to be analyzed is placed on or near the roughened metal surface. Irradiation of the sample and the roughened metal surface generates an intense SPP that the sample experiences. The intense SPP is one factor that increases the number of Raman scattered photons from the sample that are characteristic of the sample's chemical composition. Raman scattered photons are a result of photons (i.e., Stokes and anti-Stokes radiation) that are scattered inelastically from the sample.

In addition to SPPs utility in sensor and spectroscopic applications, metallic interconnects that support SPPs are currently being investigated as replacements for conventional optical interconnects, such as optical fibers and other dielectric waveguides, used in electronic devices. As the size of electronic devices continues to relentlessly decrease every few years, further increases in processor speed may be prevented by thermal and signal delay issues associated with electronic interconnection between electronic components. Optical interconnects are believed to provide one solution to signal delay problems because optical interconnects posses a large data carrying capacity compared to conventional microscale or submicroscale metal signal lines. However, widespread utilization of optical interconnects has been hampered due to a large size mismatch between nanoscale and microscale electronic components and the optical interconnects. Optical interconnects are limited in size by the fundamental laws of diffraction to about half a wavelength of light and tend to be about one or two orders of magnitude larger than nanoscale and microscale electronic components.

Replacing conventional optical and metallic interconnects with plasmonic structures has been proposed because metals commonly used in electrical interconnects, such as copper and aluminum, allow excitation of SPPs. SPP waves propagating along a plasmonic interconnect could be used to transmit data signals to and from other chips or electronic devices. Thus, plasmonic interconnects would allow for the large data carrying capacity of conventional optical interconnects, while having the nanoscale or microscale dimensions of conventional metal interconnects. Additionally, plasmonic interconnects can also allow for electrical signals to be transmitted concurrently with SPP waves to further increase processing speed.

Therefore, a need exists for developing improved nanostructures that enable coupling electromagnetic radiation to GWs supported by the nanostructures. Additionally, a need exists to reduce the size mismatch between waveguides and other components in electronic and optoelectronic devices.

SUMMARY

Various aspects of the present invention are directed to nanowires configured to couple electromagnetic radiation to GWs, methods of fabricating such nanowires, and devices incorporating such nanowires. In one aspect of the present invention, a nanowire structure is disclosed. The nanowire structure includes a substrate and at least one nanowire attached to the substrate. The at least one nanowire has a circumferential surface and a diameter that varies generally periodically along a length of the at least one nanowire. In one embodiment of the present invention, the at least one nanowire may be formed from a metallic material. In certain embodiments of the present invention, the at least one nanowire includes alternating and periodically spaced first and second metallic nanowire segments, with each first metallic nanowire segment having a different composition than each second metallic nanowire segment. In another embodiment of the present invention, a coating covers at least part of the circumferential surface of the at least one nanowire.

In another aspect of the present invention, a method of fabricating at least one nanowire is disclosed. The method includes growing the at least one nanowire on a substrate. The method further includes generally periodically varying at least one growth-process parameter during growth of the at least one nanowire so that a diameter of the at least nanowire varies generally periodically.

In yet another aspect of the present invention, a device is disclosed. The device includes a nanowire structure and at least one optical-to-electrical converter. The nanowire structure includes at least one nanowire having a length. A diameter, composition, or both may vary generally periodically along the length of the at least one nanowire. The at least one optical-to-electrical converter is operable to convert electromagnetic radiation generated, at least in part responsive to irradiation of the at least one nanowire, to an electrical signal. In certain embodiments of the present invention, the device may form part of a SERS system, an interconnect structure for chip-scale electronics, or a wavelength selective light detector.

BRIEF DESCRIPTION OF THE DRAWINGS

The drawings illustrate various embodiments of the present invention, wherein like reference numerals refer to like elements or features in different views or embodiments shown in the drawings.

FIGS. 4A through 4G are schematic side views that illustrate various stages in a method of forming a nanowire structure including nanowires having a diameter that varies periodically along a length of the nanowire.

FIG. 4H is a schematic cross-sectional view after coating the nanowires shown in FIG. 4G with a coating.

FIG. 4I is a schematic isometric view of the nanowire structure shown in FIG. 4H.

DETAILED DESCRIPTION OF VARIOUS EMBODIMENTS

Various embodiments of the present invention are directed to nanowires configured to couple electromagnetic radiation to selected GWs, methods of fabricating such nanowires, and devices incorporating such nanowires. The disclosed devices may be utilized in many diverse applications, such as SERS, wavelength selective light detectors, interconnects for chip-scale electronics, and many other applications.

Figure 1:
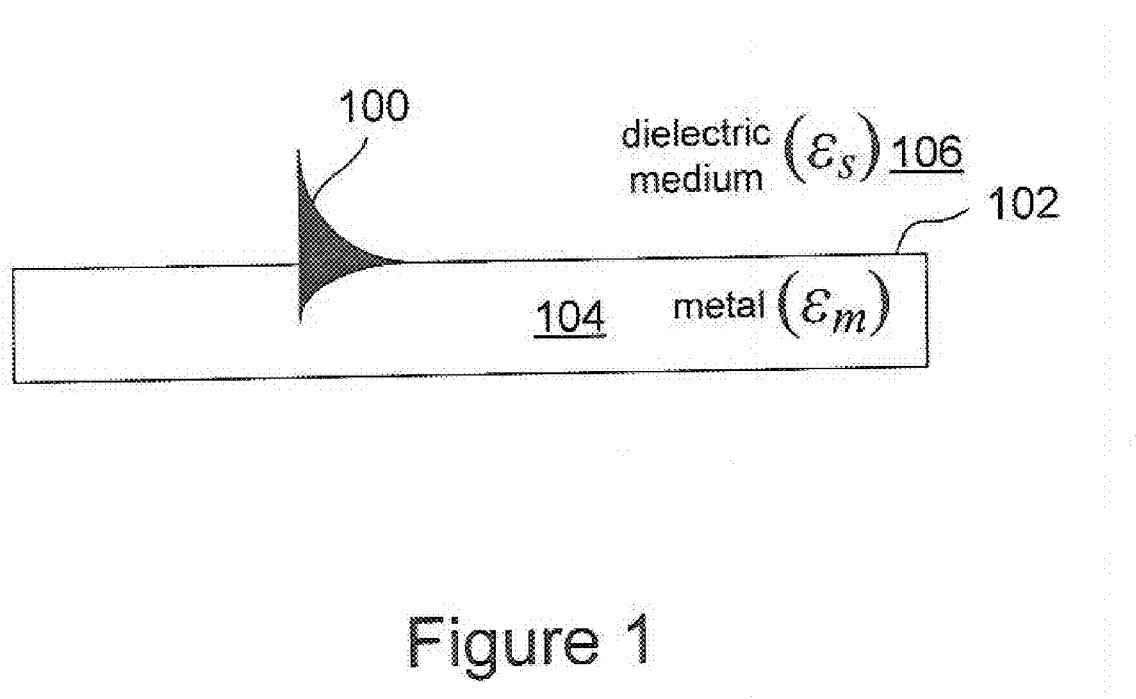
FIG. 1 is a schematic diagram illustrating propagation of a SPP wave along an interface between a metal and a dielectric medium.
Figure 2A:
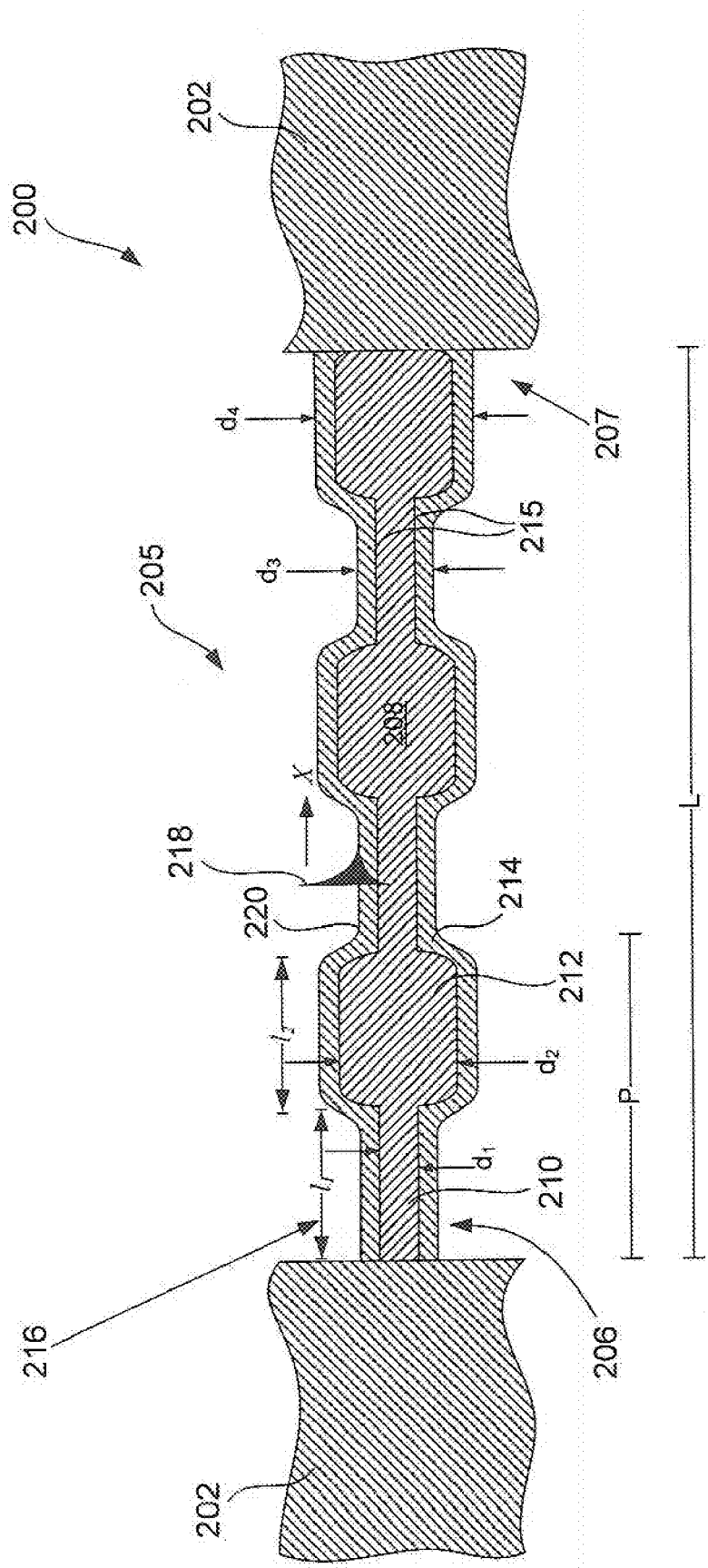
FIG. 2A is a schematic side cross-sectional view of a nanowire structure configured to couple electromagnetic radiation to a SPP wave that propagates along a length of the nanowire structure according to one embodiment of the present invention.

FIG. 2A shows a plasmonic nanowire structure 200 according to one embodiment of the present invention. The plasmonic nanowire structure 200 includes a substrate 202 having at least one nanowire structure 205 attached to the substrate 202, with the nanowire structure 205 structured to support SPPs. As used herein, a substrate may include a number of different layers, and various types of electronic and photonic devices. The nanowire structure 205 includes a proximal end portion 206 attached to one portion of the substrate 202 and a distal end portion 207 attached to an opposing portion of the substrate 202, with the proximal end portion 206 and the distal end portion 207 spaced apart a length L. The nanowire structure 205 further includes a nanowire 208 having nanowire segments 210 and 212 that are alternating and periodically spaced. Each of the nanowire segments 210 has an average diameter $d_1$ and a length $l_1$. Each of the nanowire segments 212 has an average diameter $d_2$ that is not equal to the diameter $d_1$ and a length $l_2$. For example, the diameters $d_1$ and $d_2$ may be about 1 nm to about 300 nm and the lengths $l_1$ and $l_2$ may be about 10 μm or less. As shown in FIG. 2A, the diameter of the nanowire 208 formed of the nanowire segments 210 and 212 varies periodically over a period P from a diameter $d_1$ to a diameter $d_2$.

The nanowire 208 may be formed from a number of different materials including silicon, germanium, silicon-germanium alloys, group III-V semiconductor compounds (e.g., GaAs), or another suitable material. In some embodiments of the present invention, the composition of the nanowire 208 is substantially uniform. In other embodiments of the present invention, each of the nanowire segments 210 may comprise a first semiconductor material, such as silicon, and each of the nanowire segments 212 may comprise a second semiconductor material, such as germanium or a silicon-germanium alloy, that has a different composition than the first semiconductor material. In still another embodiment of the present invention, each of the nanowire segments 210 may comprise a first metallic material, such as tin (i.e., a substantially pure metal), and each of the nanowire segments 212 may comprise a second metallic material, such as a tin alloy, that has a different composition than the first metallic material. As will be discussed in more detail below with respect to FIGS. 4A through 4I, one approach for controllably varying the diameter of the nanowire segments 210 and 212 is by controllably varying the composition of the nanowire segments 210 and 212.

Still referring to FIG. 2A, a coating 214 coats at least part of a circumferential surface 215 of the nanowire 208. For example, in the illustrated embodiment, the coating 214 may cover substantially the entire circumferential surface 215. However, in other embodiments of the present invention, the coating 214 coats only a portion of the circumferential surface 215. The coating 214 may be formed of a number of different materials that have a real, negative dielectric constant at a frequency of interest. For example, the coating 214 may be formed from a number of different electrically conductive materials, such as copper, aluminum, gold, silver, alloys of any of the preceding metals, doped semiconductor materials, or another material with a suitable electrical conductivity (e.g., a resistivity of 30 μΩ·cm or less). After coating the semiconductor nanowire 208, the diameter of the resulting nanowire structure 205 varies periodically over a period P from an average diameter $d_3$ in the regions near the nanowire segments 210 to an average diameter $d_4$ in the regions near nanowire segments 212.

The periodic variation in the diameter of the nanowire structure 205 enables coupling free-space or guided electromagnetic radiation 216 to surface plasmons of the coating 214 to generate SPPs. Thus, the coating 214 forms a generally one-dimensional metallic grating and the surface plasmons of the coating 214 may be selectively coupled to free-space or guided electromagnetic radiation of a selected wavelength or range of wavelengths. The wavelength or range of wavelengths at which electromagnetic radiation may be coupled into the surface plasmons of the coating 214 of the nanowire structure 205 may be controlled by tailoring the period P and the composition of the coating 214.

As illustrated in FIG. 2A, irradiating the proximal end portion 206 of the nanowire structure 205 with the free-space or guided electromagnetic radiation 216 couples electromagnetic radiation at a selected wavelength or range of wavelengths into the surface plasmons of the coating 214. The grating-like structure of the coating 214 diffracts the electromagnetic radiation 216, and the diffracted electromagnetic radiation having a wavevector and frequency that coincides with a wavevector and frequency of a SPP wave 218 is coupled to the surface plasmons of the coating 214. The coupling excites the SPP wave 218 that propagates along an interface 220 between the coating 214 and a surrounding medium, such as air or another medium with a real, positive dielectric constant. The SPP wave 218 propagates in a direction X along the interface 220 to the distal end portion 207 of the nanowire structure 205. Accordingly, the nanowire structure 205 having a periodically varying diameter may be used to couple free-space or guided electromagnetic radiation at a selected wavelength or range of wavelengths into the surface plasmons of the coating 214 to generate SPPs that propagate along the length of the nanowire structure 205. It is noted that when the nanowire 208 is formed from a degenerately-doped semiconductor material or a metallic material having a real, negative dielectric constant at a frequency of interest, the coating 214 may be omitted because SPPs may be excited at the circumferential surface 215.

Figure 2B:
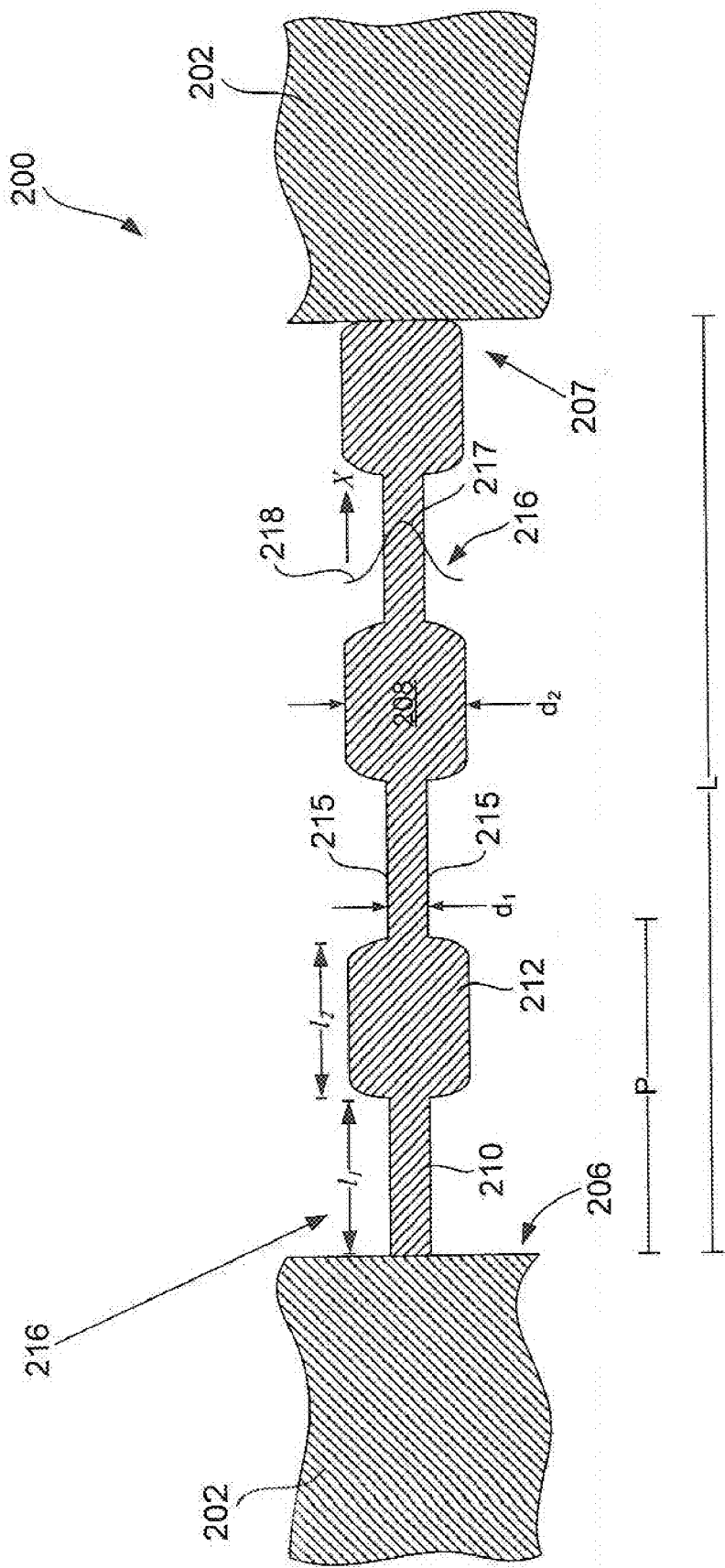
FIG. 2B is a schematic side cross-sectional view of the nanowire shown in FIG. 2A used to couple electromagnetic radiation to a GW that propagates within the nanowire.

FIG. 2B illustrates how the nanowire 208 may be used to couple the electromagnetic radiation 216 to a GW that propagates within the nanowire 208. In such an embodiment, the coating 214 shown in FIG. 2A may be omitted, and the nanowire 208 may be formed from any of the previously described semiconductor materials, such as silicon, germanium, silicon-germanium alloys, and combinations thereof so that the nanowire 208 has a real, positive dielectric constant that is greater than the dielectric constant of the medium surrounding the nanowire 208. During use, the free-space or guided electromagnetic radiation 216 irradiates the proximal end portion 206 and couples to a GW 216 that propagates within the nanowire 208 in the direction X toward the distal end portion 207. The GW 216 has a confined portion 217 that is confined within the nanowire 208 due to the nanowire 208 having a larger average dielectric constant than the surrounding medium. The GW 216 also has an evanescent portion 218 that extends outside the nanowire 208. The intensity of the evanescent portion 218 of the GW 216 decreases with distance radially away from the nanowire 208. Varying the period P of the nanowire 208 and the difference between the dielectric constants of the nanowire 208 and the surrounding medium enables controlling the wavelength or range of wavelengths of the free-space or guided electromagnetic radiation 216 that may be coupled into the nanowire 208.

Figure 3:
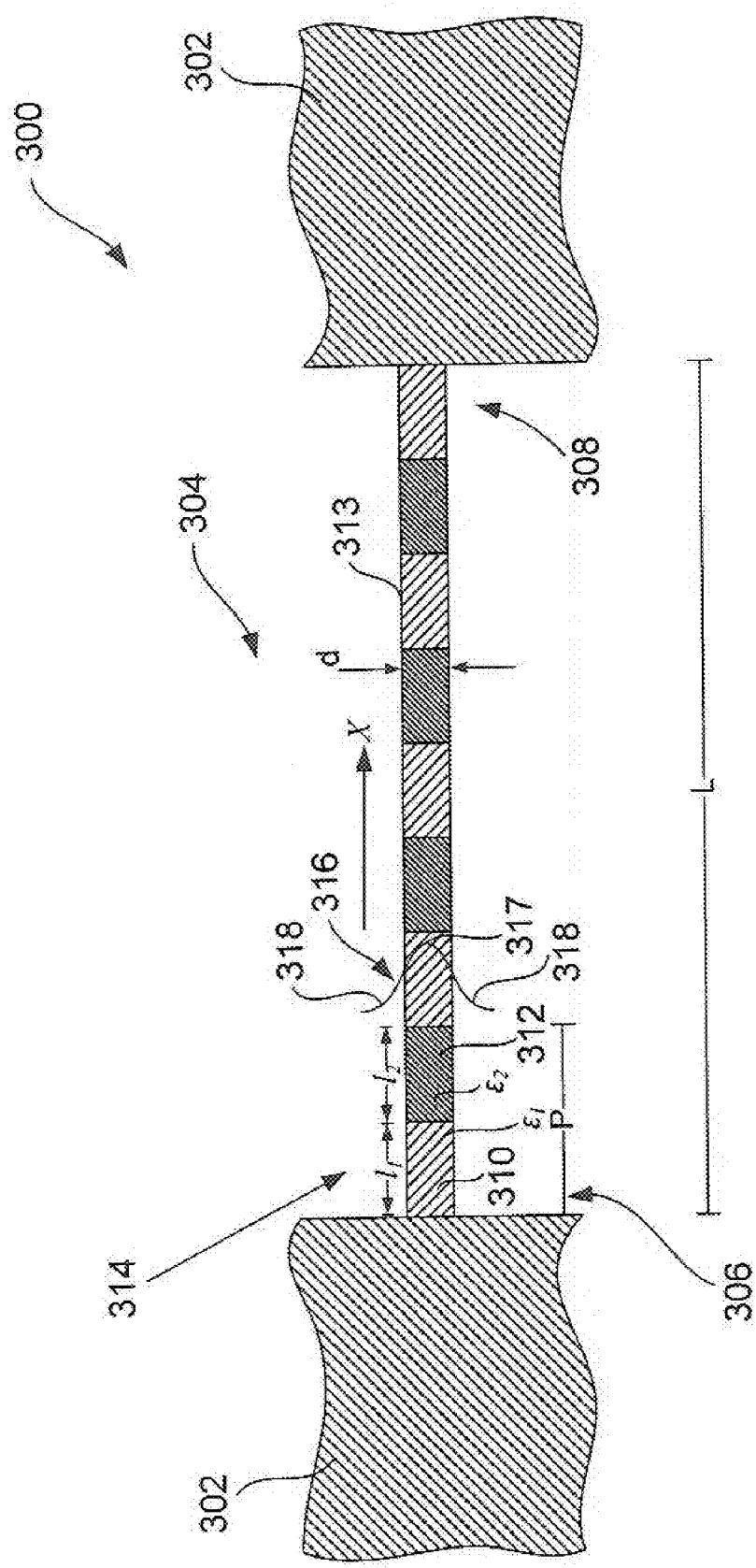
FIG. 3 is a schematic side cross-sectional view of a nanowire structure including at least one nanowire configured to couple electromagnetic radiation to a GW that propagates within the at least one nanowire according to another embodiment of the present invention.

FIG. 3 shows a nanowire structure 300 according to another embodiment of the present invention. The nanowire structure 300 includes a substrate 302 with at least one nanowire 304 attached to the substrate 302. The nanowire 304 includes a proximal end portion 306 attached to one portion of the substrate 302 and a distal end portion 308 attached to an opposing portion of the substrate 302, with the proximal end portion 306 and the distal end portion 308 spaced apart a length L. The nanowire 304 further includes nanowire segments 310 and 312 that are alternating and periodically spaced. Each nanowire segment 310 has a positive, first dielectric constant $\in_1$ and each nanowire segment 312 has a positive, second dielectric constant $\in_2$ that is different than the first dielectric constant. Each of the nanowire segments 310 has a length $l_1$ and each of the nanowire segments 312 has a length $l_2$.

The dielectric constant of the nanowire 304 may be periodically varied by forming the nanowire segments 310 and 312 with different compositions. Each of the nanowire segments 310 may comprise a semiconductor material having a first composition with the first dielectric constant $\in_1$, such as silicon, germanium, alloys thereof, III-V semiconductor compounds, doped semiconductor materials, or another suitable semiconductor material. Each of the nanowire segments 312 may comprise a semiconductor material having a second composition, with the second dielectric constant $\in_2$, that is different than the first composition. For example, each of the nanowire segments 310 may comprise a semiconductor material (e.g., silicon, germanium) and each of the nanowire segments 312 may comprise a silicon-germanium alloy. In another example, each of the nanowire segments 310 may comprise GaAs and each of the nanowire segments 312 may comprise AlGaAs. Accordingly, the composition and dielectric constant of the nanowire 304 varies periodically with a period P, while maintaining diameter d of the nanowire 304 substantially constant.

The periodically varying dielectric constant of the nanowire 304 enables coupling free-space or guided electromagnetic radiation to a GW of the nanowire 304 in a manner similar to the nanowire structure 208 shown in FIG. 2B. As illustrated in FIG. 3, free-space or guided electromagnetic radiation 314 having a selected wavelength or range of wavelengths may irradiate the proximal end portion 306 of the nanowire 304 and couple to a GW of the nanowire 304. The GW 316 propagates within the nanowire 304 in a direction X to the distal end portion 308. As shown, the GW 316 has a confined portion 317 that is confined within the nanowire 304 due to the nanowire 304 having a larger average dielectric constant than the surrounding medium. The GW 316 also has an evanescent portion 318 that extends outside the nanowire 304. The intensity of the evanescent portion 318 of the GW 316 decreases with distance radially away from the nanowire 304. Varying the period P of the nanowire 304 and the difference between the first and second dielectric constants $\in_1$ and $\in_2$ enables controlling the wavelength or range of wavelengths of free-space or guided electromagnetic radiation that may be coupled into the nanowire 304 in a manner similar to the nanowire structure 205 shown in FIG. 2A.

FIGS. 4A through 4I schematically illustrate various stages in a method of forming the nanowire structure 205 shown in FIG. 2A according to various embodiments of the present invention. A nanowire with a periodically varying diameter, such as the nanowire structure 205 shown in FIG. 2A, may be formed by varying at least one growth-process parameter. As will be described in more detail below, nanowires with a periodically varying diameter may be formed without having to use precision lithography techniques.

Figure 4A:
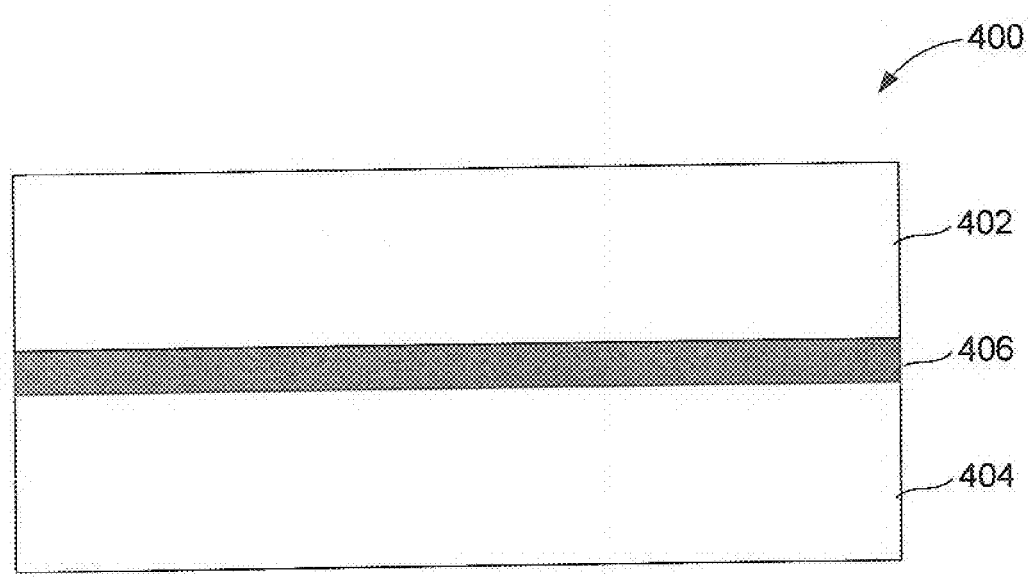
FIGS. 4A through 4I are schematic views that illustrate various stages in a method of forming a nanowire structure according to one embodiment of the present invention.

As shown in FIG. 4A, a silicon-on-insulator ("SOI") substrate 400 is provided. The SOI substrate 400 may be configured as a silicon-on-oxidized silicon substrate, silicon-on-ceramic ("SOC") substrate, silicon-on-glass ("SOG")

substrate, silicon-on-sapphire ("SOS") substrate, or any other suitable substrate. The SOI substrate 400 illustrated in FIG. 4A includes a single-crystal silicon layer 402, a substrate layer 404, and an electrically insulating layer 406 sandwiched between the silicon layer 402 and the substrate layer 404. The electrically insulating layer 406 may comprise silicon dioxide, silicon nitride, or another suitable electrically insulating layer.

Figure 4B:
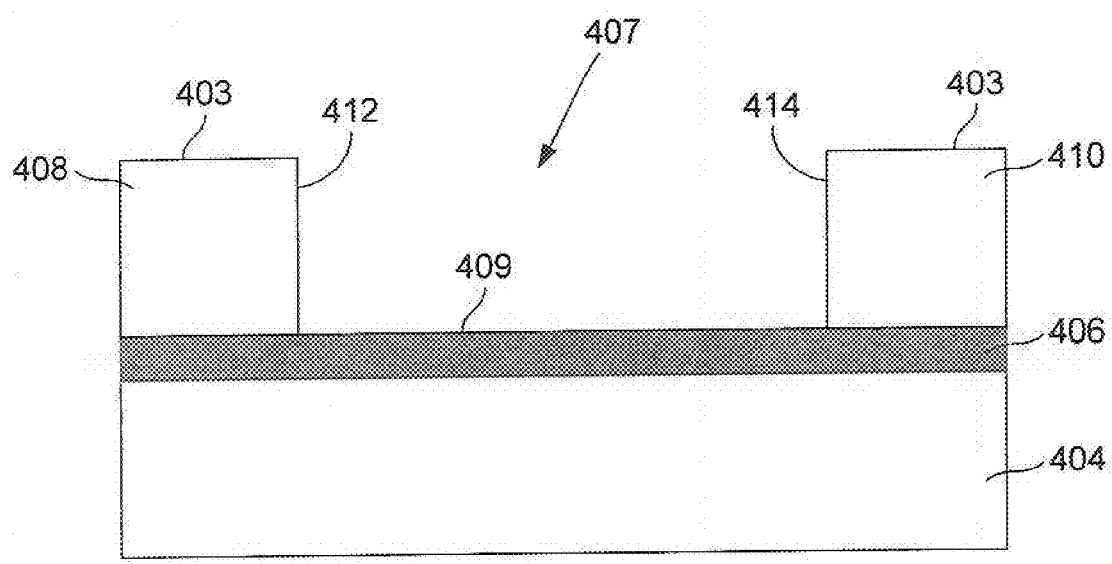

Next, as shown in FIG. 4B, a slot 407 may be formed in the single-crystal silicon layer 402 to expose a surface 409 of the electrically insulating layer 406. Posts 408 and 410 are the portions of the single-crystal silicon layer 402 that remain after forming the slot 407. The slot 407 may be formed in the single-crystal silicon layer 402 by lithographically (e.g., photolithography) patterning a resist layer applied over the single-crystal silicon layer 402 and anisotropic etching, ion beam milling, or another suitable selective material removal technique. As illustrated in FIG. 4B, the posts 408 and 410 have corresponding generally vertical sidewalls 412 and 414. An upper surface 403 of the silicon layer 402 may have a (110) crystallographic orientation and each of the sidewalls 412 and 414 may have a (111) crystallographic orientation.

Figure 4C:
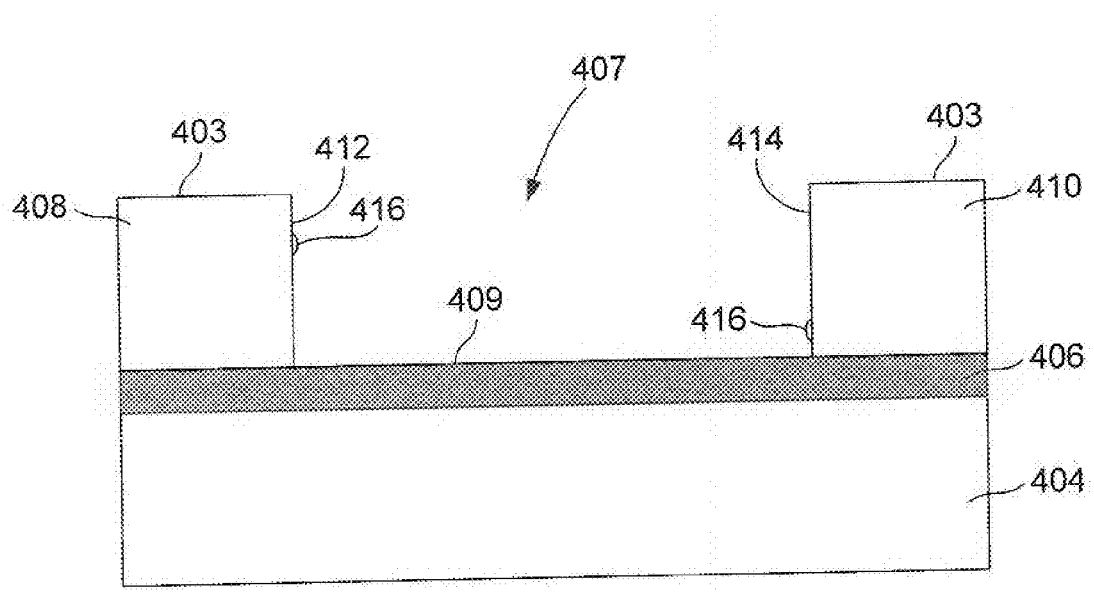

As shown in FIG. 4C, a number of metal-catalyst nanoparticles 416 may be formed on, deposited on, or in other ways provided on the sidewalls 412 and 414. Only two metal-catalyst nanoparticles 416 are illustrated in FIG. 4C for simplicity. According to one embodiment of the present invention, one or more metal-catalyst nanoparticles 416 may be selectively formed on the sidewalls 412 and 414 using an electrochemical process, a physical deposition process, or another suitable deposition process. Each of the metal-catalyst nanoparticles 416 may exhibit a diameter or lateral dimension of less than about 500 nm and more particularly the diameter or lateral dimension may be about 5 nm to about 300 nm. The metal-catalyst nanoparticles 416 may have various different compositions. For example, the metal-catalyst nanoparticles 416 may comprise gold, platinum, palladium, nickel, cobalt, titanium, alloys of any of the preceding metals, or another suitable catalytically-active material.

In one specific embodiment of the present invention, the in-process structure shown in FIG. 4B may be cleaned, if necessary, and immersed in a 1-2 mM solution of $NaAuCl_4 2H_2O$ in anhydrous ethanol to electrolessly form one or more gold nanocrystals on the sidewalls 412 and 414. The gold nanocrystals preferentially form on the sidewalls 412 and 414 instead of the exposed surface 409 of the electrically insulating layer 406 because the sidewalls 412 and 414 are generally free of an oxide layer, providing an exposed silicon surface for the gold nanocrystals to preferentially nucleate on. The upper surfaces 403 may also be covered with an insulating material, such as silicon dioxide, which prevents formation of the metal-catalyst nanoparticles 416 thereon. In another approach, any metal-catalyst nanoparticles 416 formed on the upper surfaces 403 may be removed using, for example, chemical-mechanical polishing ("CMP"). It is noted that the use of gold to form the metal-catalyst nanoparticles 416 is merely an illustrative example. Metal-catalyst nanoparticles 416 having other compositions, such as platinum-, palladium-, nickel-, cobalt-, and titanium-containing nanoparticles may also be formed using a similar electrochemical technique or another selective deposition technique (e.g., chemical vapor deposition of titanium).

In another embodiment of the present invention, the metal-catalyst nanoparticles 416 may be formed using a physical deposition process, such as electron-beam deposition, atomic-beam deposition, or molecular-beam deposition. In such deposition techniques, a thin film of material may be deposited on one or both of the sidewalls 412 and 414 by directing a flux of the material at a selected angle. Annealing the as-deposited thin film causes agglomeration of the material comprising the thin film to form metal-catalyst nanoparticles. In yet another embodiment of the present invention, the metal-catalyst nanoparticles 416 may be preferentially deposited on one or both of the sidewalls 412 and 414 by directing a flux of metal-catalyst nanoparticles at an angle relative to, for example, the sidewall 412. By relatively orienting the angle of the sidewall 412 and the direction of the flux of the metal-catalyst nanoparticles 416, the metal-catalyst nanoparticles 416 may be preferentially deposited on the sidewall 412.

Figure 4D:
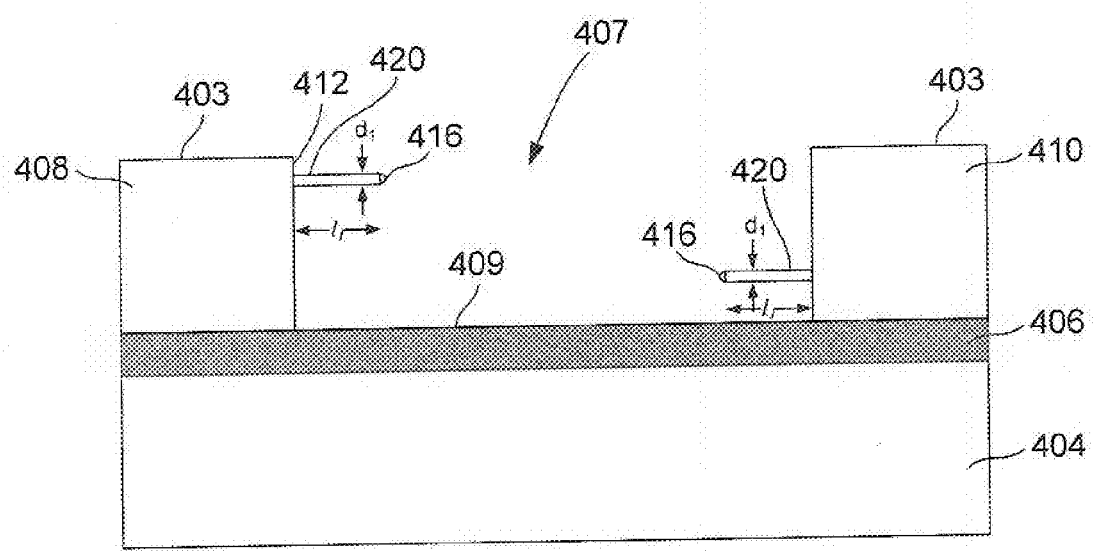

The metal-catalyst nanoparticles 416 may be used to catalyze the growth of semiconductor nanowires that have a periodically varying diameter. As shown in FIG. 4D, nanowire segments 420, each of which has an average diameter $d_1$ and a length $l_1$, may be grown by chemical vapor deposition ("CVD") in which the nanowire segments 420 grow as a result of a vapor-liquid-solid ("VLS") growth process or a vapor-solid growth process. The in-process structure shown in FIG. 4C, including the metal-catalyst nanoparticles 416, may be heated to a temperature sufficient to establish intimate contact between the metal-catalyst nanoparticles 416 and the sidewalls 412 and 414.

Still referring to FIG. 4D, next, a precursor gas for forming the nanowire segments 420 may be flowed to contact the metal-catalyst nanoparticles 416 located at ends of the nanowire segments 420 projecting from the posts 408 and 410, with the CVD chamber maintained at a first total pressure condition $P_1$ that may be about 1 torr to about 600 torr. For example, single-crystal silicon nanowire segments may be formed from a silicon-containing precursor gas, such as silane ("$SiH_4$"), a mixture of $SiH_4$ and gaseous hydrochloric acid ("HCl"), dichlorosilane ("$SiH_2Cl_2$"), or silicon tetrachloride ("$SiCl_4$"). Single-crystal germanium nanowire segments may be formed using a germanium-containing precursor gas comprising germane ("$GeH_4$"). As merely a non-limiting illustrative example, when the nanoparticles 416 are formed from gold, the nanoparticles 416 may at least partially or completely interact with the substrate on which they are deposited due to the temperature at which the CVD process is performed. By the time the precursor gas is introduced, the gold nanocrystals may be alloyed with silicon from the sidewalls 412 and 414 to form a gold-silicon alloy. Subsequently, for example, when the precursor gas is introduced, silicon atoms from the precursor gas may dissolve in the gold-containing droplets until the saturation limit of silicon in the gold-containing droplet is reached. Then, excess silicon atoms precipitate out of the gold-containing droplets onto the sidewalls 412 and 414 and grow epitaxially thereon. The nanowire segments 420 may progressively grow as a single-crystal silicon nanowire due to continued dissolving of silicon atoms from the precursor gas and deposition onto an end of the growing nanowire segment adjacent to the gold-containing droplet. In addition to or as an alternative to the silicon atoms dissolving in the gold-containing droplet, the silicon atoms may diffuse around the gold-containing droplet and, initially, grow epitaxially at an interface between the sidewalls 412 and 414 and the gold-containing droplet and/or an interface between one of the growing nanowire segment and the gold-containing droplet.

In other embodiments of the present invention, the nanowire segments 420 may be grown by a vapor-solid growth process. For example, when each of the metal-catalyst nanoparticles 416 comprises a titanium nanocrystal, the CVD deposition of silicon may be carried out at a temperature in which the nanoparticles 416 are not partially or completely melted. In such an embodiment, silicon atoms from the precursor gas may dissolve in the titanium nanocrystals until the saturation limit in titanium is reached. In addition to or as an alternative to the atoms from the precursor gas dissolving in the titanium nanocrystals, the silicon atoms may diffuse around the titanium nanocrystals and, initially, precipitate and grow epitaxially at the interface between the sidewalls 412 and 414 and the titanium nanocrystals to initiate nanowire growth. Further catalyzed epitaxial growth at the tip of the nanowire elongates the nanowire.

Figure 4E:
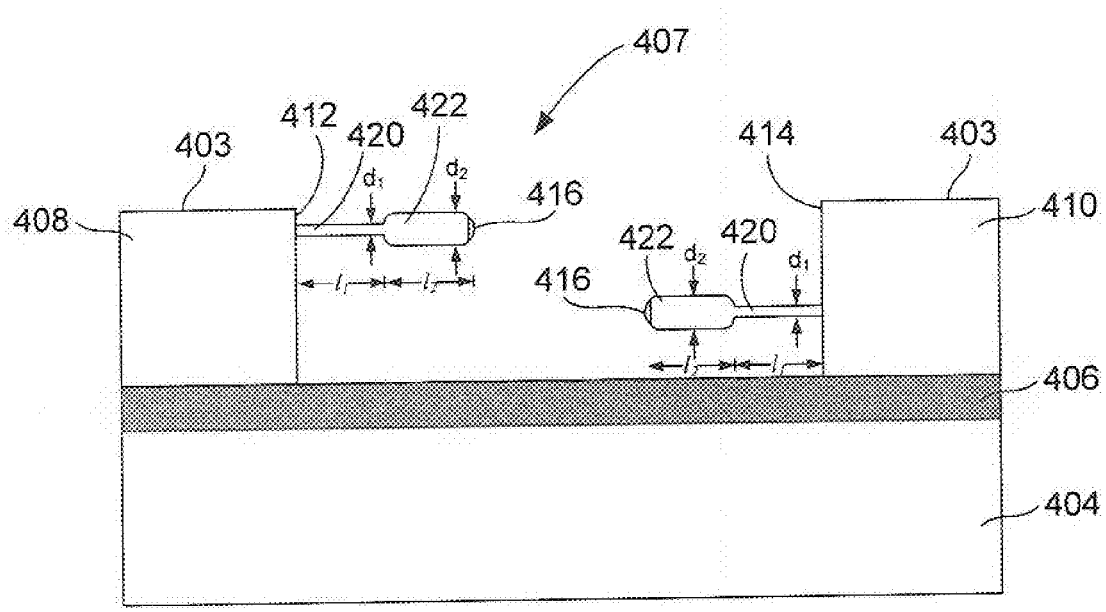

Following formation of the nanowire segments 420, a growth-process parameter is varied. According to one embodiment of the present invention, the total pressure of the CVD chamber may be altered from the total pressure $P_1$ to a different total pressure $P_2$ of, for example, between about 1 torr to about 600 torr. Many commercially available CVD systems have the capability to rapidly vary the total pressure within a CVD chamber within, for example, a minute or less. The diameter of a nanowire segment is dependent upon the diameter of the metal-catalyst nanoparticle used to catalyze the growth thereof and process conditions, such as total pressure of the CVD chamber. Thus, altering the total pressure of the CVD chamber, enables controllably altering the diameter of the nanowire segment. As shown in FIG. 4E, nanowire segments 422 may be grown with an average diameter $d_2$ that is greater than the diameter $d_1$ of the nanowire segments 420 by altering the total pressure of the CVD chamber from the total pressure $P_1$ to a different total pressure $P_2$. Length $l_2$ of each of the nanowire segments 422 may be controlled by the growth rate and growth time. Growth of the nanowire segments 422 may proceed by any of the growth processes described above with respect to the semiconductor nanowire segments 420. As illustrated in FIG. 4E, each of the nanowire segments 422 grows as an extension of a corresponding one of the nanowire segments 420.

Figure 4F:
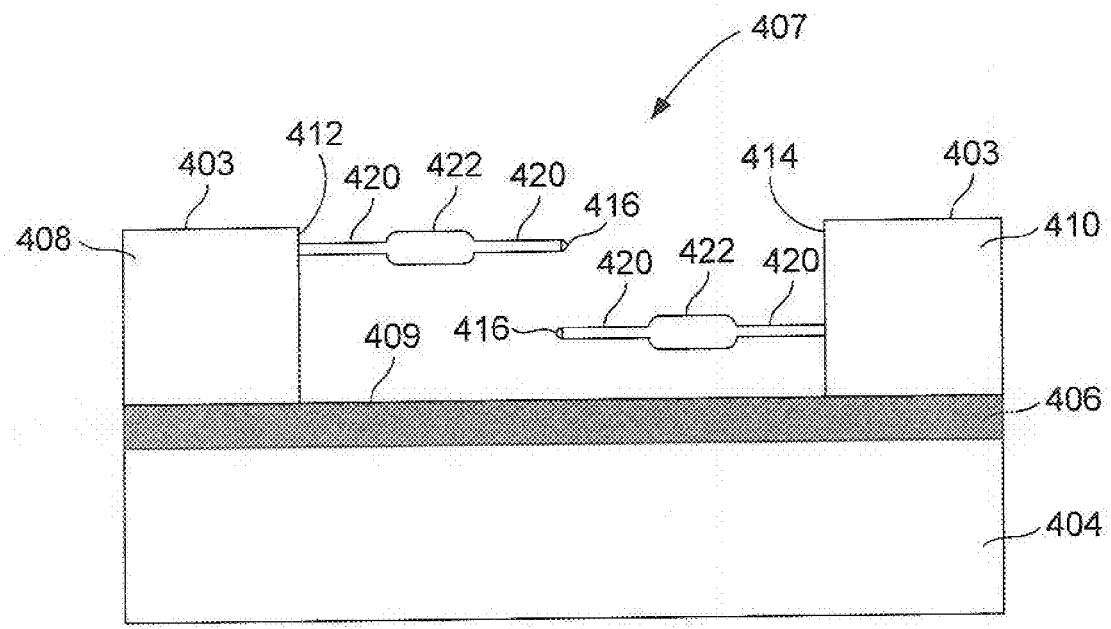
Figure 4G:
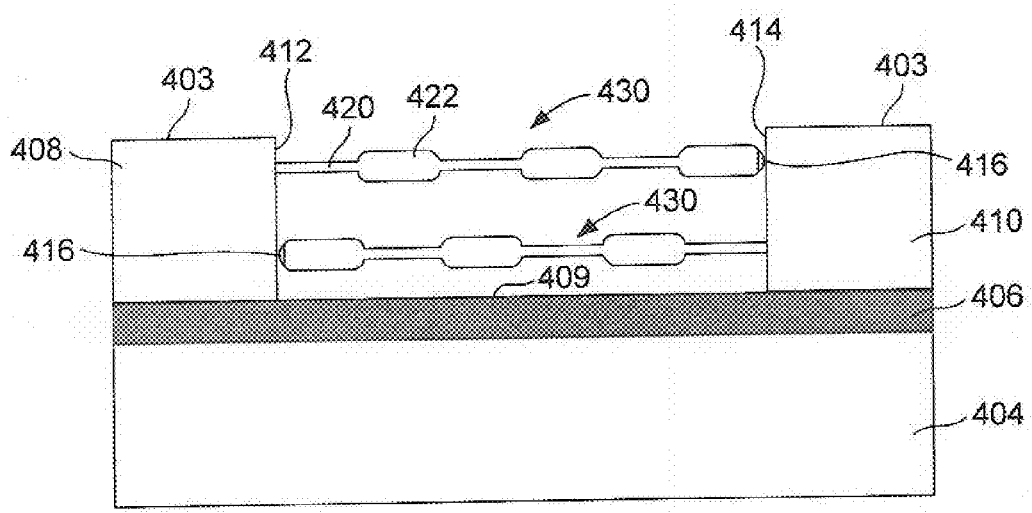

Following growth of the nanowire segments 422, the total pressure of the CVD chamber may again be altered to the total pressure $P_1$ in order to grow additional nanowire segments 420. As shown in FIG. 4F, the additional nanowire segments 420 are grown on corresponding previously grown nanowire segments 422 shown in FIG. 4E. The process of varying the total pressure of the CVD chamber to controllably vary the diameter of the nanowire segments may be repeated, as needed, to grow additional nanowire segments 420 and 422 until completed nanowires 430 are formed that span between the sidewalls 412 and 414, as illustrated in FIG. 4G. The nanowires 430 so formed exhibit a controlled periodic variation in diameter, with each of the nanowires 430 formed of alternating and periodically spaced nanowire segments 420 and 422 having a diameter that varies from a diameter $d_1$ to a diameter $d_2$.

In other embodiments of the present invention, instead of altering the total pressure of the CVD chamber to vary the diameter of each nanowire 430, the diameter of each nanowire 430 may be controllably varied by growing the nanowire segments 420 with a different composition than the composition of the nanowire segments 422. For example, each of the nanowire segments 420 may comprise silicon and each of the nanowire segments 422 may comprise germanium or a silicon-germanium alloy grown by CVD. In other embodiments of the present invention, each of the nanowire segments 420 may comprise a first metallic material (e.g., tin) and each of the nanowire segments 422 may comprise a second metallic material (e.g., an alloy of tin) that is compositionally different than the first metallic material. It is noted that when the composition is varied periodically, other CVD growth parameters may also have to be properly selected (e.g., total pressure of the CVD chamber, partial pressure of the precursor gases, and/or growth temperature).

Figure 4H:
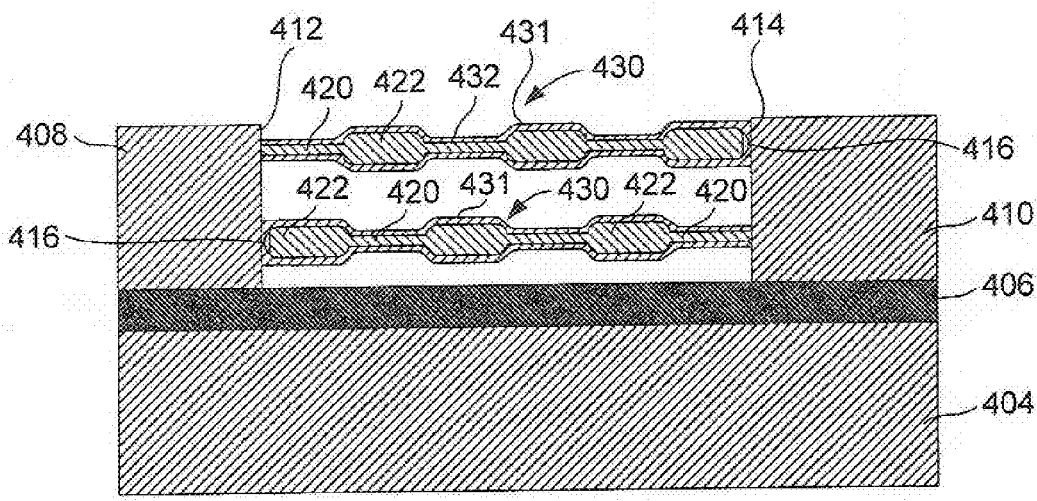
Figure 4I:
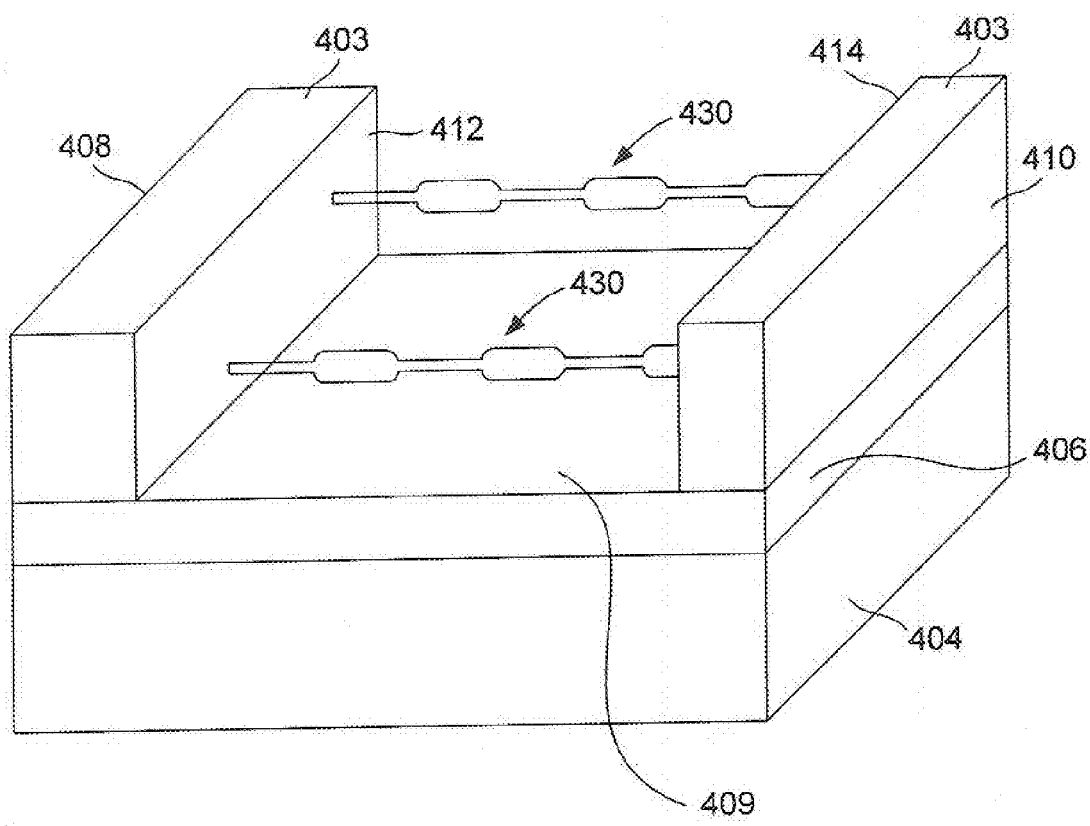

Regardless of the particular technique used to vary the diameter of the nanowires 430, as shown in FIG. 4H, if desired, a coating 432 may be deposited on each of the nanowires 430 using CVD, a physical vapor deposition process ("PVD") (e.g., evaporation or sputtering), or another suitable technique to form nanowire structures 434. The coating 432 may be made from the same materials as the coating 214 shown in FIG. 2A. CVD deposition of the coating 432 may generally coat substantially the entire circumferential surface 431 of each of the semiconductor nanowires 430. PVD deposition of the coating 432 may generally coat only a portion of the circumferential surface 431 that is exposed to the flux of coating material. As previously discussed, if the nanowires 430 are formed from degenerately-doped semiconductor materials or metallic materials, the coating 432 may be omitted. FIG. 4I shows a schematic isometric view of the nanowire structure with the nanowire structures 434 spanning between the sidewalls 412 and 414 of corresponding posts 408 and 410.

Figure 5:
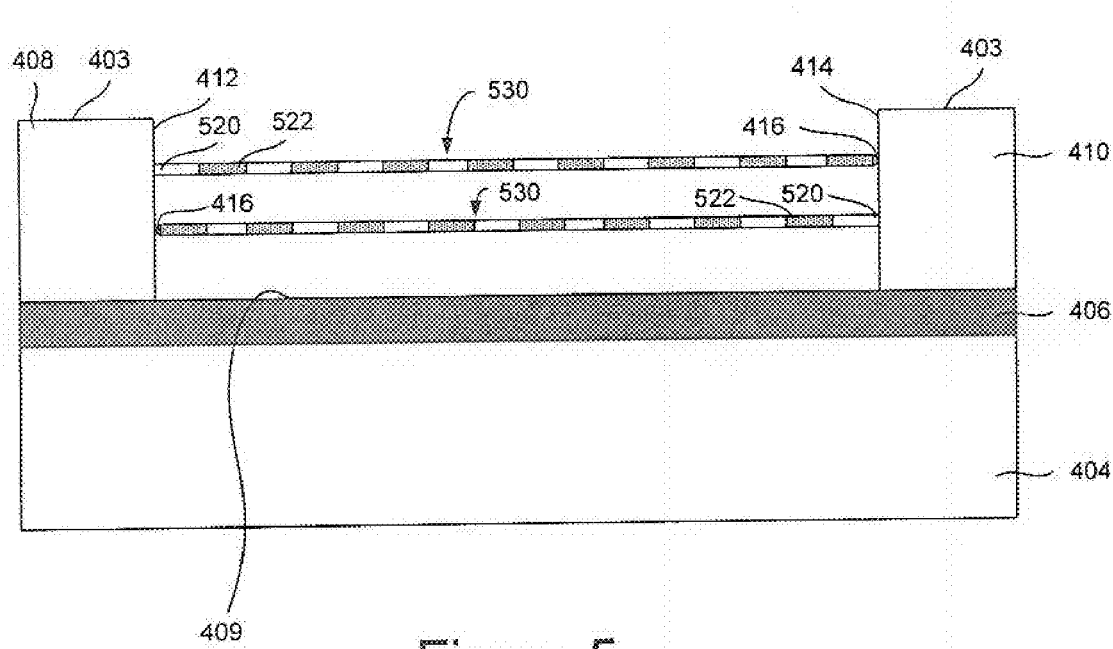
FIG. 5 is a schematic side view of a nanowire structure according to another embodiment of the present invention.

An embodiment of a method according to the present invention for forming a nanowire with a periodically varying composition is described with respect to FIG. 5. In the interest of brevity, the nanowires are shown formed on the in-process structure shown in FIG. 4C, and the same reference numerals are used to refer to the same features or elements of the in-process structure shown in FIG. 4C. As shown in FIG. 5, nanowires 530 may be formed to span between the sidewalls 412 and 414 of corresponding posts 408 and 410. One of the nanowires 530 grows on the sidewall 412 and the other one of the nanowires 530 grows on the sidewall 414. During growth of the nanowires 530, the composition of the precursor gas used for forming the nanowires 530 is varied periodically to form alternating and periodically spaced nanowire segments 520 and 522, while still maintaining a substantially uniform diameter d. The nanowire segments 520 and 522 may be grown using a vapor-liquid-solid growth process or a vapor-solid growth process, as previously described with respect to FIGS. 4A through 4I, catalyzed using the metal-catalyst nanoparticles 416.

In one embodiment of the present invention, each of the nanowire segments 520 may be formed from silicon grown by CVD using $SiH_4$, a mixture of $SiH_4$ and $HCl$, $SiH_2Cl_2$, or $SiCl_4$. The nanowire segments 522 may be formed from, for example, germanium grown by CVD using a $GeH_4$ precursor gas. Accordingly, alternating and periodically spaced silicon nanowire segments and germanium nanowire segments may be formed by periodically varying the precursor gas composition from a silicon-containing gas to a germanium-containing gas in combination with control of other growth parameters, such as total pressure of the CVD chamber and temperature. For example, growth of silicon nanowire segments may be effected at a temperature of about 600° Celsius and growth of germanium nanowire segments may be effected at a temperature of about 330° Celsius. In another embodiment of the present invention, each of the nanowire segments 520 may comprise silicon grown by CVD using any of the aforementioned silicon-containing gases, and each of the nanowire segments 522 may comprise a silicon-germanium alloy grown by CVD using a mixture of any of the aforementioned silicon-containing precursor gases and $GeH_4$.

Figure 6:
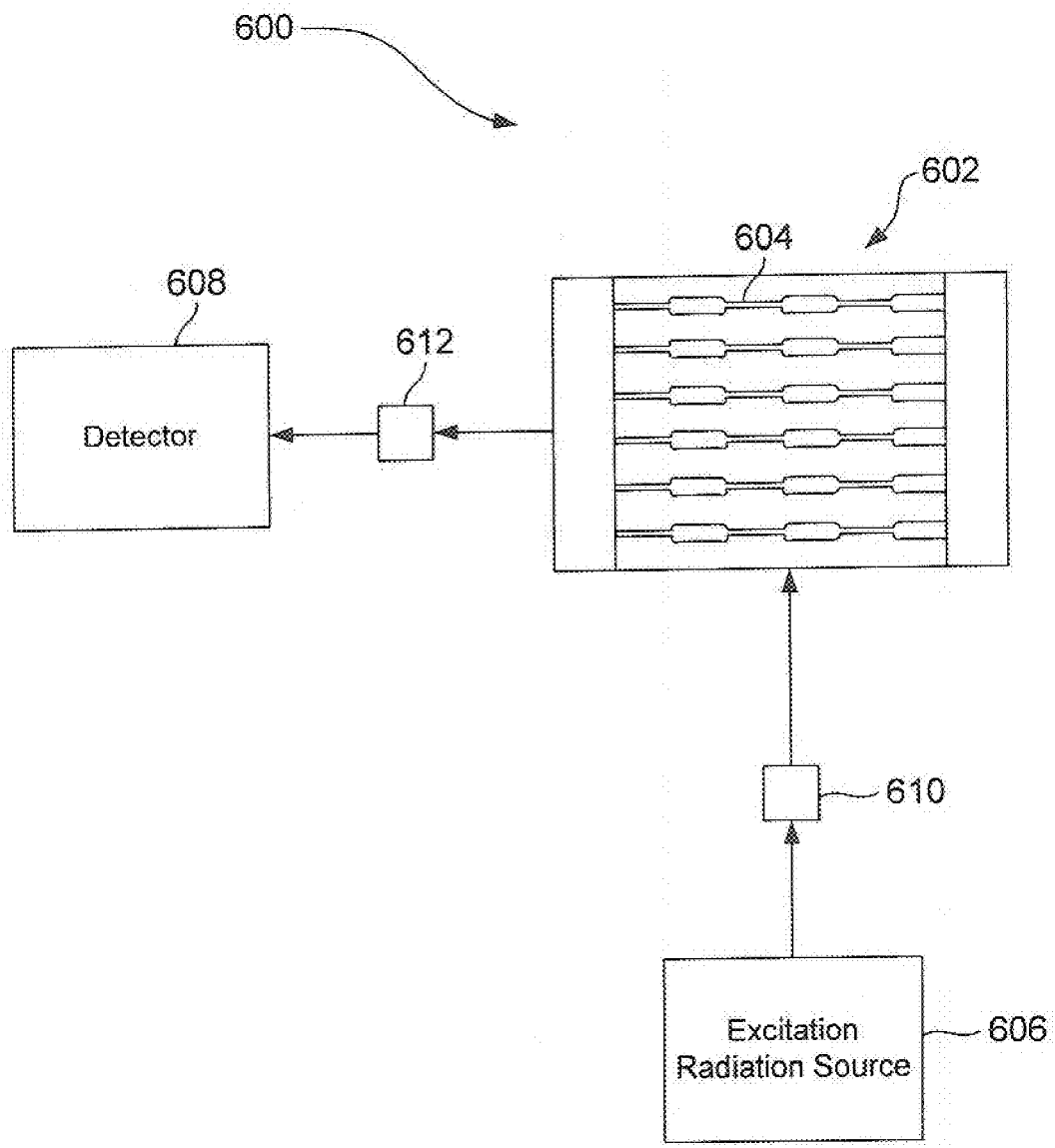
FIG. 6 is a functional block diagram of a SERS system according to one embodiment of the present invention.

Any of the aforementioned embodiments of nanowires and nanowire structures shown and described with respect to FIGS. 2A-2B, 3, 4H, and 5 may be used in a number of different devices. For example, FIG. 6 shows a functional block diagram of a SERS system 600 according to one embodiment of the present invention. The SERS system 600 includes a nanowire structure 602 having a number of regularly-spaced nanowires 604 configured to couple electromagnetic radiation to GWs, as previously described. Each of the nanowires 604 shown in FIG. 6 is illustrated with a diameter that varies periodically. However, in other embodiments, some or all of the nanowires may have a composition that varies periodically. The SERS system 600 further includes an excitation radiation source 606 and a detector 608. The SERS system 600 may also include various optical components 610 positioned between the excitation radiation source 600 and the nanowire structure 602, and various optical components 612 positioned between the nanowire structure 602 and the detector 608.

The excitation radiation source 606 may include any suitable source for emitting radiation at the desired wavelength, and may be capable of emitting a tunable wavelength of radiation. For example, commercially available semiconductor lasers, helium-neon lasers, carbon dioxide lasers, light emitting diodes, incandescent lamps, and many other known radiation-emitting sources may be used as the excitation radiation source 606. The electromagnetic radiation emitted by the excitation radiation source 606 may have any suitable wavelength for analyzing an analyte using SERS. For example, the excitation radiation source 606 may emit electromagnetic radiation having a range of wavelengths from about 350 nm to about 10 μm. The excitation radiation emitted by the excitation radiation source 606 may be delivered directly from the source 606 to the nanowire structure 602. Alternatively, collimation, filtration, and subsequent focusing of the excitation radiation may be performed by optical components 610 before the excitation radiation impinges on the nanowire structure 602.

The nanowire structure 602 may enhance the Raman signal of the analyte. In other words, irradiation of the nanowires 604 of the nanowire structure 602 by excitation radiation from the excitation radiation source 606 generates GWs (e.g., SPPs or other GWs), as previously described, that may increase the number of photons inelastically scattered by an analyte molecule positioned near or adjacent to the nanowires 604. For example, when the nanowires 604 are configured to couple electromagnetic radiation from the excitation radiation source 606 to SPP waves, the SPP waves may enhance the Raman signal. When the nanowires 604 are configured to couple electromagnetic radiation from the excitation radiation source 606 to GWs that propagate within the nanowires 604, such as the GWs 216 and 316 shown in FIGS. 2B and 3, an evanescent portion of the GW may enhance the Raman signal.

The Raman scattered photons may be collimated, filtered, or focused with optical components 612. For example, a filter or a plurality of filters may be employed, either as part of the structure of the detector 608, or as a separate unit that is configured to filter the wavelength of the excitation radiation, thus allowing only the Raman scattered photons to be received by the detector 608. The detector 608 receives and detects the Raman scattered photons and may include a monochromator (or any other suitable device for determining the wavelength of the Raman scattered photons) and a device such as, for example, a photomultiplier for determining the quantity of Raman scattered photons (intensity). In general, the Raman scattered photons are scattered isotropically, being scattered in all directions relative to the nanowire structure 602. Thus, the position of the detector 602 relative to the nanowire structure 602 is not particularly important. However, the detector 608 may be positioned at, for example, an angle of ninety degrees relative to the direction of the incident excitation radiation to minimize the intensity of the incident excitation radiation that may be incident on the detector 608.

To perform SERS using the SERS system 600, a user may provide an analyte molecule or molecules adjacent to the nanowires 604 of the nanowire structure 602. The analyte and the nanowire structure 602 are irradiated with excitation electromagnetic radiation from the source 606. Then, Raman scattered photons scattered by the analyte are detected by the detector 608.

Figure 7:
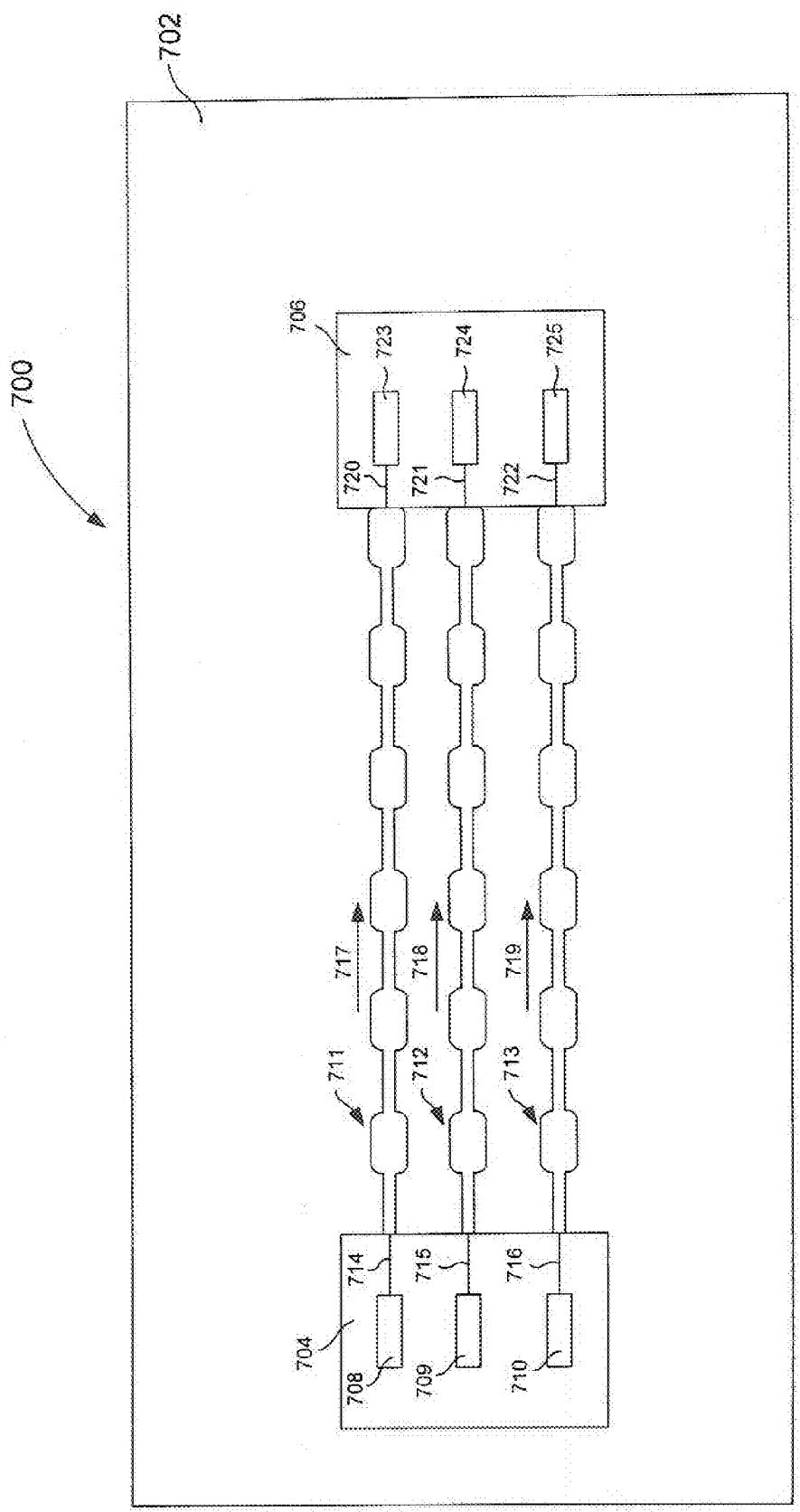
FIG. 7 is a schematic plan view of a semiconductor device that utilizes any of the disclosed nanowires and nanowire structures as interconnects according to one embodiment of the present invention.

The disclosed nanowires and nanowire structures may also be used as interconnects for communicating electrical signals. FIG. 7 shows a semiconductor device 700 that utilizes interconnects according to one embodiment of the present invention. The semiconductor device 700 includes a substrate 702 having device circuitry 704 and 706, such as CMOS circuitry, formed within the substrate 702. For example, the device circuitry 704 may be associated with processing functions and the device circuitry 706 may be associated with memory functions. The semiconductor device 700 also includes a number of electrical-to-optical converters 708-710 (e.g., edge emitting laser diodes) coupled to corresponding interconnects 711-713 via corresponding waveguides 714-716. The interconnects 711-713 may be configured as any of the previously described nanowires and nanowire structures configured to support SPPs or other GWs. The electrical-to-optical converters 708-710 are operable to convert electrical signals transmitted from the device circuitry 704 to corresponding optical signals. During operation, the converted optical signals may be evanescently coupled to corresponding interconnects 711-713 via the corresponding optical waveguides 714-716. For example, each optical waveguide 714-716 may be a waveguide integrated with the circuitry formed in the substrate 702, a tapered optical fiber, or another suitable waveguide. An end of each of the optical waveguides 714-716 may overlie or abut a corresponding interconnect 711-713.

During operation, the converted optical signals are coupled to GWs of the interconnects 711-713 to excite GWs 717-719, which propagate along the length of the corresponding interconnects 711-713. The GWs 717-719 may evanescently couple to corresponding waveguides 720-722 that transmit the GWs 717-719 to corresponding optical-to-electrical converters 723-725 and convert the GWs 717-719 to corresponding electrical signals. Each of the optical-to-electrical converters 723-725 may be, for example, a PIN photodiode or another suitable type of optical-to-electrical converter. Each of the optical-to-electrical converters 723-725 is coupled to the device circuitry 706, and the converted electrical signals may be transmitted from the optical-to-electrical converters 723-725 to the device circuitry 706 for further processing, if desired.

It is noted that the semiconductor device 700 is merely one embodiment of a device that may utilize interconnects formed from the nanowires disclosed herein. Interconnects may be used to communicate between different chips or substrates, and the nanowires structured to support GWs disclosed herein may be used in many different applications where a metallic or optical interconnect is used.

Figure 8:
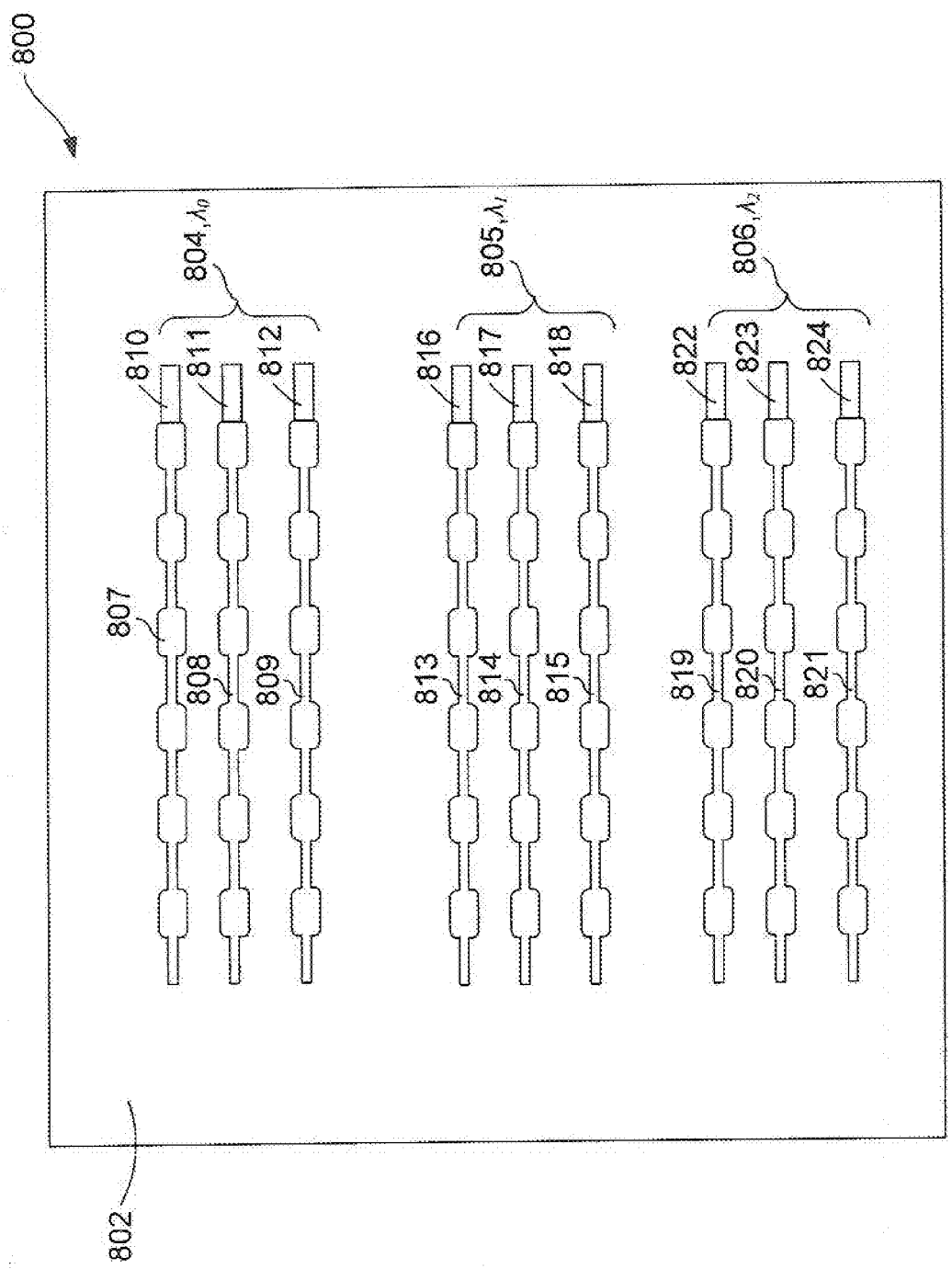
FIG. 8 is a schematic plan view of a wavelength selective light detector that utilizes any of the disclosed nanowires and nanowire structures according to yet another embodiment of the present invention.

FIG. 8 shows a wavelength selective light detector ("WSLD") 800 that may also utilize any of the disclosed nanowires and nanowire structures configured to couple electromagnetic radiation to GWs according to yet another embodiment of the present invention. The WSLD 800 includes a substrate 802 carrying detection modules 804-806. Each of the detection modules 804-806 includes nanowires structured so that GWs thereof may be coupled to electromagnetic radiation of a different selected wavelength. The detection module 804 includes a number of nanowires 807-809 each of which is configured to couple electromagnetic radiation at wavelength $\lambda_1$ to a GW. The detection module 805 includes a number of nanowires 813-815 each of which is configured to couple electromagnetic radiation at wavelength $\lambda_2$ to a GW. The detection module 806 includes a number of nanowires 819-821 each of which is configured to couple electromagnetic radiation at wavelength $\lambda_3$ to a GW.

In operation, electromagnetic radiation having a range of wavelengths that may include electromagnetic radiation at wavelengths $\lambda_1$, $\lambda_2$, and $\lambda_3$ irradiates the detection modules 804-806 of the WSLD 800. Electromagnetic radiation having the wavelength $\lambda_1$ may couple to GWs of at least a portion of the nanowires 807-809, and each GW propagates along a length of a corresponding one of the nanowires 807-809. Each GW is received by a corresponding optical-to-electrical converter 810-812, such as a PIN photodiode, that generates an electrical signal. Electromagnetic radiation having the wavelength $\lambda_2$ may couple to GWs of at least a portion of the nanowires 813-815, and each GW propagates along a length of a corresponding one of the nanowires 813-815. Each GW is received by a corresponding optical-to-electrical converter 816-818 that generates an electrical signal. Similarly, electromagnetic radiation having a wavelength $\lambda_3$ may couple to GWs of at least a portion of the nanowires 819-821, and each GW propagates along a length of a corresponding one of the nanowires 819-821. Each GW is coupled to a corresponding optical-to-electrical converter 822-824 that generates an electrical signal. Accordingly, electrical signals generated by the optical-to-electrical converters 822-824 are indicative of electromagnetic radiation having a wavelength at $\lambda_1$, $\lambda_2$, and/or $\lambda_3$. In certain embodiments of the present invention, the GWs propagating along the nanowires may be coupled to corresponding optical-to-electrical converters via optical waveguides, such as optical fibers or dielectric waveguides embedded in the substrate 802.

The WSLD 800 may be used to detect electromagnetic radiation having a number of different wavelengths. In particular, the disclosed nanowires and nanowire structures may be used for detecting terahertz ("THz") frequency electromagnetic radiation that is difficult to detect with many conventional optical-to-electrical converters. The WSLD 800 may be used to detect low-levels of THz electromagnetic radiation because of the high intensity of the GWs propagating along the nanowires and collected by the optical-to-electrical converters.

Although the present invention has been described in terms of particular embodiments, it is not intended that the present invention be limited to these embodiments. Modifications within the spirit of the present invention will be apparent to those skilled in the art. For example, in another embodiment of the present invention, the nanowires having a periodic variation in diameter, composition, or both do not need to be supported at both ends as illustrated in the FIGS. 2A-2B and 3A. Instead, in other embodiments of the present invention, the nanowires may be attached to a substrate at only one end by, for example, growing them on a surface of a substrate. Additionally, in embodiments of the present invention in which a diameter of a nanowire varies periodically, the diameter may be periodically varied by growing the nanowire under low-temperature conditions that promote growth instabilities. Similarly, the composition of the nanowire may be varied periodically by exploiting instabilities in the growth process. Such growth instabilities may result in a nanowire with a periodically varying diameter without having to alter other growth conditions, such as total pressure within a chamber, nanowire composition, etc.

The foregoing description, for purposes of explanation, used specific nomenclature to provide a thorough understanding of the present invention. However, it will be apparent to one skilled in the art that the specific details are not required in order to practice the present invention. The foregoing descriptions of specific embodiments of the present invention are presented for purposes of illustration and description. They are not intended to be exhaustive of or to limit the present invention to the precise forms disclosed. Many modifications and variations are possible in view of the above teachings. The embodiments are shown and described in order to best explain the principles of the present invention and its practical applications, to thereby enable others skilled in the art to best utilize the present invention and various embodiments with various modifications as are suited to the particular use contemplated. It is intended that the scope of the present invention be defined by the claims and their equivalents:

The invention claimed is:

1. A nanowire structure, comprising:
   a substrate;
   at least one nanowire attached to the substrate, the at least one nanowire having a circumferential surface and a diameter that varies generally periodically along a length of the at least one nanowire; and
   a coating covering at least part of the circumferential surface of the at least one nanowire.

2. The nanowire structure of claim 1 wherein the coating covers substantially the entire circumferential surface of the at least one nanowire.

3. The nanowire structure of claim 1 wherein the coating comprises a metallic material or a doped semiconductor material.

4. The nanowire structure of claim 1 wherein the at least one nanowire comprises first and second nanowire segments alternating and generally periodically spaced along the length, the first nanowire segment having a first average diameter and the second nanowire segment having a second average diameter that is not equal to the first average diameter.

5. The nanowire structure of claim 4 wherein:
   the first nanowire segments are spaced from each other by a first longitudinal dimension of about 10 µm or less;
   the second nanowire segments are spaced from each other by a second longitudinal dimension of about 10 µm or less.

6. The nanowire structure of claim 4 wherein each of the first and second nanowire segments comprises one of:
   a semiconductor material; and
   a metallic material.

7. The nanowire structure of claim 4 wherein each of the first nanowire segments is compositionally different than each of the second nanowire segments.

8. The nanowire structure of claim 1 wherein the at least one nanowire has a substantially uniform composition.

9. A nanowire structure, comprising:
   a substrate; and
   at least one metallic nanowire attached to the substrate, the at least one metallic nanowire having a diameter that varies generally periodically along a length of the at least one metallic nanowire.

10. The nanowire structure of claim 9 wherein the at least one metallic nanowire comprises first and second nanowire segments alternating and generally periodically spaced along the length, the first nanowire segment having a first average diameter and the second nanowire segment having a second average diameter that is not equal to the first average diameter.

11. The nanowire structure of claim 10 wherein each of the first and second nanowire segments comprises one of:
a substantially pure metal; and
an alloy.

12. The nanowire structure of claim 10 wherein each of the first nanowire segments is compositionally different than each of the second nanowire segments.

13. A method of fabricating at least one nanowire, comprising:
growing the at least one nanowire on a substrate; and
generally periodically varying at least one growth-process parameter during growth of the at least one nanowire so that a diameter of the at least nanowire varies generally periodically.

14. The method of claim 13 wherein generally periodically varying at least one growth-process parameter during growth of the at least one nanowire comprises generally periodically varying a total pressure of a chamber in which the at least one nanowire is grown.

15. The method of claim 13 wherein generally periodically varying at least one growth-process parameter during growth of the at least one nanowire comprises generally periodically varying the composition of a precursor gas used to form the at least one nanowire.

16. The method of claim 13 wherein the at least one nanowire comprises first and second nanowire segments alternating and generally periodically spaced along the length, the first nanowire segment having a first average diameter and the second nanowire segment having a second average diameter that is not equal to the first average diameter.

17. The method of claim 13, further comprising coating at least part of a circumferential surface of the at least nanowire with a coating.

18. A device, comprising:
a nanowire structure including at least one nanowire having a length, at least one of a diameter and a composition varying generally periodically along the length of the at least one nanowire; and
at least one optical-to-electrical converter operable to convert electromagnetic radiation generated, at least in part responsive to irradiation of the at least one nanowire, to an electrical signal,
wherein the at least one nanowire comprises first and second nanowire segments alternating and generally periodically spaced along the length, the first nanowire segment having a first average diameter and the second nanowire segment having a second average diameter that is not equal to the first average diameter.

19. The device of claim 18:
further comprising an excitation source operable to emit excitation electromagnetic radiation having at least one wavelength selected to couple to a guided wave that propagates along the length of the at least one nanowire; and
wherein the electromagnetic radiation comprises Raman-scattered light, and further wherein the at least one optical-to-electrical converter is configured to receive the Raman-scattered light scattered from an analyte positioned at least proximate to the at least one nanowire.

20. The device of claim 18:
further comprising at least one excitation source operable to emit an optical signal corresponding to a device electrical signal generated by semiconductor device circuitry, the optical signal irradiating a first end portion of the at least one nanowire to generate the electromagnetic radiation comprised of a guided wave that propagates along the length of the at least one nanowire to a second end portion distal from the first end portion; and
wherein the at least one optical-to-electrical converter is positioned to receive the guided wave and convert the guided waves to the electrical signal.

21. The device of claim 18 wherein the at least one nanowire comprises a number of nanowires arranged in nanowire sets, each of the nanowire sets configured to be selectively coupled to electromagnetic radiation at a different wavelength.

22. The device of claim 18 wherein the nanowire structure comprises a coating covering at least part of a circumferential surface of the at least one nanowire.

23. The device of claim 18 wherein the at least one nanowire comprises first and second nanowire segments alternating and generally periodically spaced along the length, each of the first nanowire segments has a different composition and dielectric constant than that of each of the second nanowire segments.

* * * * *